United States Patent [19]

Wetzel et al.

[11] Patent Number: 4,994,093
[45] Date of Patent: Feb. 19, 1991

[54] METHOD OF PRODUCING METHANOL SYNTHESIS GAS

[75] Inventors: Rolf Wetzel, Heiligenhaus; Bernhard Firnhaber, Essen, both of Fed. Rep. of Germany

[73] Assignee: Krupp Koppers GmbH, Essen, Fed. Rep. of Germany

[21] Appl. No.: 550,133

[22] Filed: Jul. 6, 1990

[30] Foreign Application Priority Data

Jul. 10, 1989 [DE] Fed. Rep. of Germany ....... 3922612

[51] Int. Cl.⁵ .......................... C10J 3/08; C10K 1/02; C10K 1/04; C01B 3/14
[52] U.S. Cl. .................................. 48/197 R; 252/373; 423/655; 518/703
[58] Field of Search ...................... 48/197 R, 202, 206, 48/210, DIG. 2; 252/373; 423/655, 656; 518/703

[56] References Cited

U.S. PATENT DOCUMENTS

| | | |
|---|---|---|
| 2,870,096 | 1/1959 | Baumann ............................. 252/323 |
| 3,069,249 | 12/1962 | Herbert ............................. 48/197 R |
| 4,075,831 | 2/1978 | McGann ............................. 48/197 R |
| 4,248,604 | 2/1981 | Woldy et al. ..................... 48/197 R |
| 4,254,094 | 3/1981 | Hegarty ............................ 423/655 |
| 4,279,622 | 7/1981 | Jones et al. ..................... 48/197 R |
| 4,338,292 | 7/1982 | Duranleau et al. .............. 423/655 |
| 4,597,776 | 7/1986 | Ullmann et al. ................. 423/655 |
| 4,617,051 | 10/1986 | Knop et al. ..................... 48/197 R |
| 4,704,137 | 11/1987 | Richter ............................ 423/655 |

Primary Examiner—Peter Kratz
Attorney, Agent, or Firm—Michael J. Striker

[57] ABSTRACT

In accordance with a method of producing of methanol synthesis gas from a partial oxidation crude gas, the gas is cooled after a waste heat boiler of a gasifier by adding a converted circulating gas in a quenching zone. The resulting gas mixture is dedusted and then separated into a product gas partial stream and a circulating gas partial stream. The product gas partial stream is supplied after corresponding gas treatment to the synthesis reactor while the circulating gas partial stream is subjected to a CO-conversion and supplied back to the quenching zone.

11 Claims, 1 Drawing Sheet

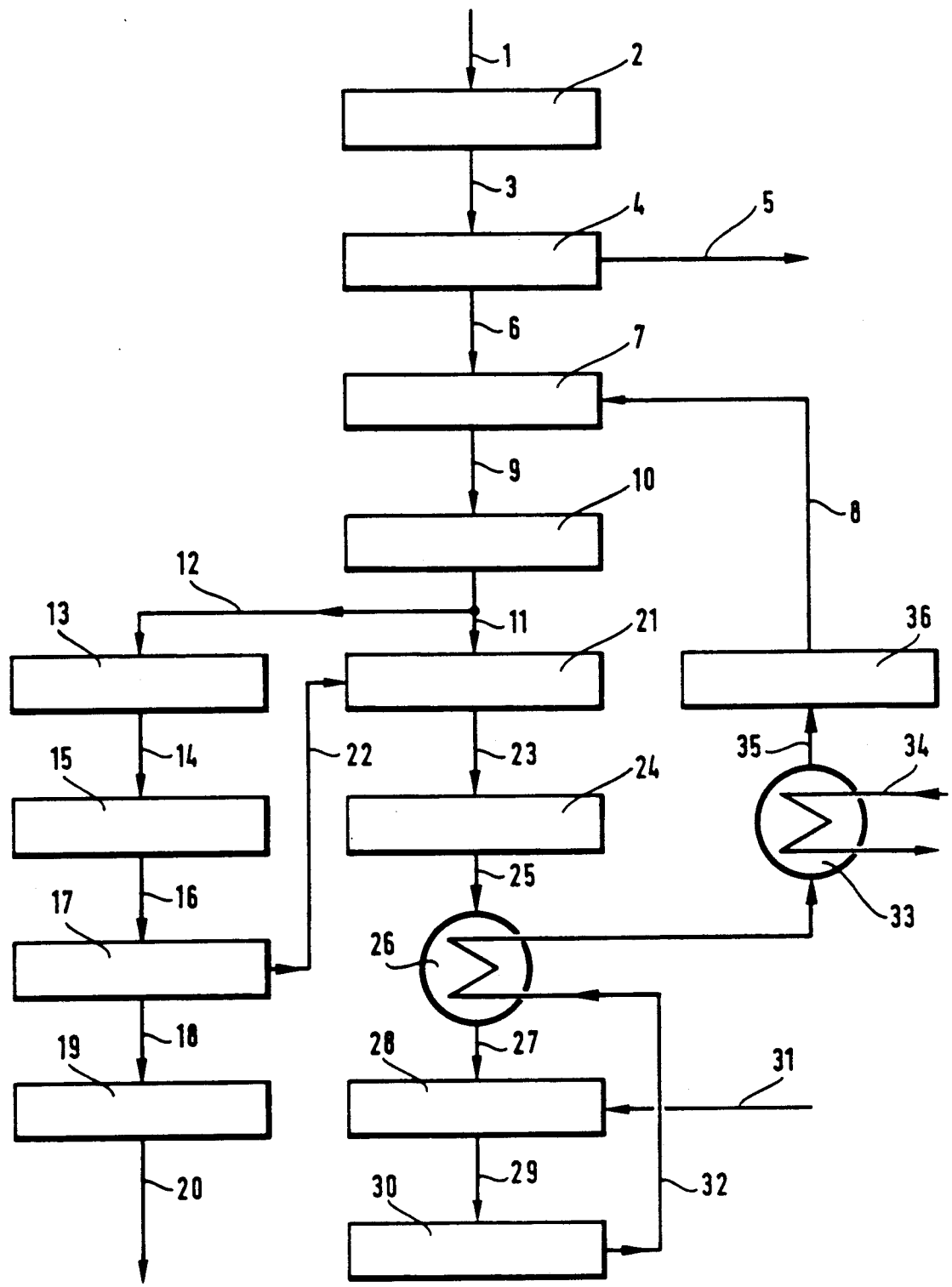

METHOD OF PRODUCING METHANOL SYNTHESIS GAS

BACKGROUND OF THE INVENTION

The present invention relates to a method of producing methanol synthesis gas.

More particularly, it relates to a method of producing methanol synthesis gas with a ratio of carbon monoxide to hydrogen defined by the desired synthesis reaction, by gasification (partial oxidation) of fine grained to dust-like fuels at temperatures above the slag melting point. The produced partial oxidation gas is indirectly cooled in a waste heat boiler located after the gasifier with production of steam, and then is subjected to dedusting, a catalytic CO-conversion, and a desulfurization.

Methods of producing of methanol synthesis gas of the above mentioned general type are known in the art. The partial oxidation crude gas produced during the gasification of fine-grained to dust-like fuels contains, depending on the composition of the used fuels and on the reaction conditions of the gasification, a ratio of carbon monoxide to hydrogen which can lie within the range between 1:1 to 2.7:1. However, for the methanol synthesis a methanol synthesis gas is required whose ratio of carbon monoxide to hydrogen must lie within the region of 0.4:1 to 0.5:1. For arriving at these values it is necessary to remove from the gas excessive CO by the CO-conversion reaction $$CO + H_2O \rightarrow H_2 + CO_2$$

with production of hydrogen. Various methods are known for producing the methanol synthesis gas from partial oxidation crude gas. When the catalyst used for the converting reaction is not sulfur resistant, the desulfurization of the gas is performed in many cases also before the conversion and not after the conversion. For the conversion itself it is required that the gas to be converted is loaded with hydrogen before entering the converting reactor and freed from excessive steam after the conversion. So-called moisturizing-demoisturizing systems are known for this purpose. During utilization of sulfur resistant conversion catalysts the loading of the partial oxidation crude gas with hydrogen can be however performed so that it is sprayed directly into the hot gas before the dedusting, and after the conversion the excessive steam is again condensed from the gas. A condensate return into the hot partial oxidation crude gas is however possible only to a limited extent when the gas must be dedusted in a dry process. Depending on the used methods of moisturizing and demoisturizing of the gas, in each case significant heat quantities in low temperature region must be withdrawn with the excess steam condensate. Simultaneously intensive heat exchange for the heating of the gas and the condensation of the excessive steam require considerable apparatus expenses.

SUMMARY OF THE INVENTION

Accordingly, it is an object of the present invention to provide a method of producing methanol synthesis gas which avoids the disadvantages of the prior art.

More particularly, it is an object of the present invention to provide a method of producing methanol synthesis gas in which the above mentioned energy and apparatus disadvantages are eliminated.

It is also an object of the present invention to provide such a method of producing of methanol synthesis gas in which simultaneously the total efficiency of the methanol recovery from fine-grained to dust-like fuels is significantly increased and the construction of the total installation is simplified.

In keeping with these objects and with others which will become apparent hereinafter, one feature of the present invention resides, briefly stated, in a method of producing of methanol synthesis gas with a ratio of carbon monoxide to hydrogen defined by the desired synthesis reaction, by gasification (partial odixation) of fine-grained to dust-like fuels at temperatures above the slag melting point, with indirect cooling of the produced partial oxidation crude gas in a waste heat boiler arranged after a gasifier with a steam generation, and with a subsequent dedusting, a catalytic CO-conversion, and a desulfurization, which is characterized by the following new features:

(a) a partial oxidation crude gas is cooled after the waste heat boiler with addition of converted circulating gas, (b) the produced gas mixture is subjected to a dry dedusting, (c) then a separation of the gas mixture is performed into a product as partial stream and a circulating gas partial stream, (d) the product gas partial stream is subjected to a further cooling, a subsequent gas washing for removing of residual dust and other impurities, a final cooling for water steam condensation, and a desulfurization and $CO_2$ removal, and then supplied to the synthesis reactor, (e) the circulating gas partial stream is saturated with utilization of the condensate from the final cooling of the product gas partial stream and washed at dew point of the gas, (f) the so purified circulating gas partial stream, for adjusting the required molar ratio of carbon monoxide to hydrogen, is subjected to a CO-conversion in the presence of a sulfur resistant catalyst, and (g) the converted circulating gas, after cooling up close to its water steam dew point and a respective condensing, is mixed with the partial oxidation crude gas in the stage a.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view showing a flow diagram of a method of producing of methanol synthesis gas in accordance with the present invention.

DESCRIPTION OF THE PREFERRED EMBODIMENTS

In accordance with the present invention methanol synthesis gas is produced in accordance with a method in which a ratio of carbon monoxide to hydrogen is defined for desired synthesis reaction, and gasification (partial oxidation) of fine-grained to dust-like fuels is performed at temperatures above the slag melting point, and the produced partial oxidation crude gas is indirectly cooled in a waste heat boiler after the gasifier with steam generation, and then subjected to a dedusting, a catalytic CO-conversion and a desulfurization.

In accordance with the novel features of the present invention, the partial oxidation crude gas is again cooled after the waste heat boiler by addition of converted circulating gas, the produced gas mixture is subjected to a dry dedusting, then a separation of the gas mixture into a product gas partial stream and a circulating gas partial stream is performed. The product gas partial stream is subjected to a further cooling, a subsequent gas washing for removing of residual dust nd other impurities, a final cooling for water steam condensation, and a desulfurization and $CO_2$ removal, and then supplied to the synthesis reactor. The circulating gas partial stream is saturated with water steam with the utilization of the condensate from the final cooling of the product gas partial stream and washed at dew point of the gas. The thusly purified circulating gas partial stream, for adjustment of the required molar ratio of carbon monoxide to hydrogen, is subjected to a CO-conversion in the presence of a sulfur resistant catalyst. The converted circulating gas after cooling close to a water steam dew point and respective condensation, is mixed with the partial oxidation crude gas in the first mentioned stage.

In other words, during the inventive process the partial oxidation crude gas which was cooled before the waste heat boiler to a temperature between 600° and 1,450° C., preferably between 800° and 1,200° C., is mixed with the converted circulating gas, so that the temperature of the produced gas mixture is lowered to the value between 200° and 800° C., preferably between 300° and 450° C. At this temperature the gas mixture is subjected to a dry dedusting and then separated into a product gas partial stream and a circulating gas partial stream. During this separation the circulating gas partial stream after its conversion is mixed with the partial oxidation crude gas after the waste heat boiler, and the resulting gas mixture must have the desired composition of the methanol synthesis gas. The separation of the mixture gas after the dry dedusting is performed in such a manner that the circulating gas partial stream has x-time volume of the product gas partial stream, wherein $$x = \frac{1}{\mu} \left[ \frac{\left(\frac{1}{r_s} + 1\right)}{\left(\frac{1}{r} + 1\right)} - 1 \right]$$

$\mu$ is the CO-conversion value in the CO-conversion or in other words the obtained ratio of converted carbon monoxide to used carbon monoxide. r is the molar ratio of the carbon monoxide to hydrogen in partial oxidation crude gas, and $r_s$ is the molar ratio of carbon monoxide to hydrogen in desired synthesis gas.

After the separation both gas partial streams are treated separately. The product gas partial stream is subjected, after a preferably indirect precooling, to a gas washing (water washing) for residual dedusting and ammonia and halogen removal, so that after the final cooling to be desulfurized in a known manner and to be freed of $CO_2$. Then this partial stream is available for the synthesis and can be introduced into the methanol synthesis reactor. The condensate produced during the final cooling of the product gas partial stream is used for extensive saturation of the circulating gas partial stream.

The circulating gas partial stream after the separation of the gas mixture is brought in contact with the condensate from the final cooling of the product gas partial stream and in some cases with additional water steam, and therefore the ratio of the carbon monoxide to hydrogen required for the performance of the converting reaction is adjusted. The CO-conversion is performed in the presence of sulfur resistant catalysts and between 60 and 95%, preferably between 80 and 95%, of the supplied carbon monoxide is converted.

Finally, the converted gas, after corresponding cooling and condensation, is supplied to the first stage of the process and then mixed with the partial oxidation crude gas.

The method in accordance with the present invention is illustrated in the flow diagram which shows respective apparatus parts required for understanding of the process. All auxiliary devices, such as for example an additional heat exchanger, pumps, valves and not important material streams are not shown. The flow diagram also does not show the details of the preceding gasification installation and the subsequent methanol synthesis since these process steps are not the object of the present invention. It is to be understood that these process steps as well as additional steps of the inventive process can be performed with known apparatus parts and aggregates.

In accordance with the process of the invention, the used fuel is supplied through a supply conduit 1 to a gasifier 2, in which the gasification (partial oxidation) of the fuel is performed under the conventional reaction conditions or with the use of known gasifier constructions. The gasifier 2 can be formed as an air flow gasifier, in which the gasification of the used fuel is performed under a pressure of more 30 bar at temperatures between 1,300° and 2,000° C. The produced partial oxidation crude gas leaves the gasifier through a conduit 3 and reaches a waste heat boiler 4 which in practice in many instances can be assembled with the gasifier 2 to form a structural unit. In the waste heat boiler 4 the partial oxidation crude gas is cooled to a temperature between 600° and 1,450° C., preferably between 800° and 1,200° C. The waste heat steam produced in this manner is withdrawn through a conduit 5 and can be supplied for a further utilization. From the waste heat boiler 4 the gas with the corresponding temperature flows through a conduit 6 to a quenching zone 7. In the quenching zone the partial oxidation crude gas is mixed with a converted circulating gas which is supplied through a conduit 8, and therefore is simultaneously cooled. The resulting gas mixture must have a temperature between 200° and 800° C., preferably between 200° and 450° C. With this temperature the gas mixture is supplied through the conduit 9 to a dry dedusting 10 and released there extensively from entrained fine dust. After the dry dedusting 10 a gas stream $\dot{V}m$ discharging through a conduit 11 is separated into two partial streams, namely a product gas partial stream $\dot{V}p$ and a circulating gas partial stream $\dot{V}k$ so that the following equation is obtained:

$$\dot{V}m = \dot{V}p + \dot{V}k$$

The stationary region during CO-conversion of the circulating gas $$\dot{V}k = x \cdot \dot{V}p$$

The factor x will be illustrated hereinbelow.

The product gas partial stream $\dot{V}p$ is withdrawn through the conduit 12 from the conduit 11 and supplied to a cooler 13 in which the gas is indirectly cooled. Subsequently it is supplied through a conduit 14 to a wet washing 15 (water washing). Here the gas is completely dedusted and in some cases freed from available ammonia and halogen compounds. Then the gas flows through a conduit 16 to a final cooler 17 and cools there to the temperature with which it must be desulfurized. For this purpose the gas is supplied through a conduit 18 to an acid gas wash 19. This is normally performed with the utilization of suitable chemically and/or physically operating washing solutions In addition to the sulfur compounds the $CO_2$ as well as other acid ingredients are removed from the gas. For the desulfurization of the gas other processes can be used, for example the dry desulfurization. After the acid gas wash 19 the gas has a composition and purity which are suitable for the synthesis and can be supplied through a conduit 20 to a not shown methanol synthesis reactor.

The circulating gas partial stream $\dot{V}k$ is supplied during this through the conduit 11 into a saturator 21, and the condensate produced in the final cooler 17 is also applied to the saturator 21 through a conduit 22. This condensate is used for water steam saturation of the circulating gas. Subsequently, the gas passes in a wet wash 24 and washed at dew point temperature. After this the gas is supplied to a heat exchanger 26 through a conduit 25. Here in indirect heat exchange with the converted gas from the converting reactor 30, the heating of the gas is performed to the starting temperature of the converting reaction which lies normally above 270° C. The correspondingly heated gas passes through a conduit 27 to a saturator 28 and mixed with the required water steam. The water steam is supplied through a conduit 31 in the saturator 28. This water steam can be a steam from the waste heat boiler 4. The saturated gas flows through a conduit 29 to a converting reactor 30, in which the CO-conversion is performed in one step or two steps in the presence of sulfur resistant catalysts. For this purpose known commercial catalysts can be used, such as for example kobalt-/molybdenum as active components.

The converted gas is withdrawn through a conduit 32 and cooled in the heat exchanger 26 and in a final cooler 33 to a temperature close to the dew point. A cooling pipe system 34 of the final cooler 33 can be used for prewarming of the supply water for the waste boiler 4. At the end of the cooling the converted gas is supplied through a conduit 35 to a compressor 36, in which it is condensed to a required degree and supplied back through the conduit 8 into quenching zone 7.

In accordance with a modification of the inventive method which is not shown in the flow diagram the wet washers 15 and 24 can operate with the same washing water circulation, in that a washing water partial stream can be withdrawn from the wet wash 24 and released from solid particles as well as from its salt load. Then the purified washing water is supplied into the saturator 21. Thereby a waste water is eliminated.

The inventive method can be performed in correspondence with the thermodynamic boundary conditions and with the performance of the CO-conversion with a technically feasible CO-conversion rate $\mu$, for example with a carbon monoxide conversion substantially under 100%. Lower carbon monoxide conversion rates require an increase of the separation ratio of the circulating gas to the product gas. A region of the carbon monoxide conversion from 60% to 95% is especially suitable with consideration of the efficient frame conditions provided for example by apparatus and machine costs and energy prices. Operational conditions, such as change in fuel quality, charge exchange, partial charge and other influences, can influence the gas composition. The continuous analytic monitoring of the molar $CO/H_2$ ratio in the product gas partial stream is important in such a case to perform a fast correction of the product gas composition by regulating the separation ratio of the circulating gas to the product gas.

A further regulating possibility resides in that apart of the circulating gas, for example from 0 to 1.0 $Nm^3$ per kg of water free carbon, for example 0.3–0.6 $Nm^3$ per kg of water free carbon, is supplied back into the burner of the gasifier 2 and used there instead of water steam for temperature moderation in the gasifier 2. Here the circulating gas is supplied through a central lance into the burner, and the lance is surrounded by two annular spaces. The coal dust is supplied through the inner annular space and the gasifying oxygen is supplied through the outer annular space.

With the partial return of the circulating gas into the burner, the quantity of oxygen is reduced in correspondence with the supplied carbon dioxide and water steam so that the gasification output is not influenced.

The efficiency of the inventive method is demonstrated hereinbelow by specific examples. A stone coal in water free condition with the following composition is used:

| | | |
|---|---|---|
| C | 76.6 | volume % |
| H | 5.0 | volume % |
| O | 8.8 | volume % |
| N | 1.3 | volume % |
| S | 0.3 | volume % |
| Ash | 7.5 | volume % |
| (Cl | 0.17 | volume %) (contained in ash) |

It is gasified in an air flow gasifier with drying coal dust supply (carrier agent nitrogen) with oxygen without addition of steam. The resulting partial oxidation crude gas in a quantity of 2.07 $Nm^3$/kg coal has an entrance to the quenching zone at a temperature of 1,100° C. the following composition:

| | | |
|---|---|---|
| CO | 67.9 | volume % |
| $H_2$ | 26.5 | volume % |
| $CO_2$ | 0.3 | volume % |
| $N_2$ | 4.7 | volume % |
| $H_2S$ | 0.2 | volume % |
| HCl | 0.05 | volume % |
| $H_2O$ | 0.3 | volume % |

For producing of methanol synthesis gas the partial oxidation crude gas is mixed with converted circulating gas of the following composition:

| | | |
|---|---|---|
| CO | 2.7 | volume % |

-continued

|  |  |
|---|---|
| $H_2$ | 42.3 volume % |
| $CO_2$ | 29.8 volume % |
| $N_2$ | 2.2 volume % |
| $H_2S$ | 0.1 volume % |
| HCl | 0.0 volume % |
| $H_2O$ | 22.9 volume % |

It is added with at a conversion ratio $\mu$ of 0.8 in a quantity of 7.6 $Nm^3$ in the quenching zone.

The resulting gas mixture has the following composition:

|  |  |
|---|---|
| CO | 16.6 volume % |
| $H_2$ | 38.9 volume % |
| $CO_2$ | 23.5 volume % |
| $N_2$ | 2.7 volume % |
| $H_2S$ | 0.15 volume % |
| HCl | 0.01 volume % |
| $H_2O$ | 18.1 volume % |

With carbon monoxide/hydrogen ratio $r_x$ desired for the methanol synthesis gas of $$r_s = 0.427$$

The gas mixture is dedusted at a temperature of 400° C. in a dry process and subsequently separated in the product gas partial stream with a quantity of 3.52 $Nm^3/kg$ $coal_{wf}$ and the circulating partial gas stream with a quantity of 6.15 $Nm^3/kg$ $coal_{wf}$.

With the above mentioned carbon monoxide/hydrogen ratio r of the partial oxidation crude gas of 2.56, the separation ratio of circulating gas to product gas $x = 1.75$.

The product gas partial stream is further treated as described hereinabove. The condensate produced during the final cooling of the product gas is used in a quantity of 0.51 kg $H_2O/kg$ $coal_{wf}$ for saturating of the circulating gas partial stream. This partial stream is also further treated as described hereinabove. Additional hydrogen in a quantity of maximum 1.0 kg/kg $coal_{wf}$ at a temperature of 300° C. is added to the gas in some cases before the conversion for adjusting the desired water steam/carbon monoxide ratio. At this temperature the saturated gas is supplied to the conversion reactor. At the end of the conversion the heated gas is cooled in the above described manner to a temperature of approximately 160° to 170° C. and then supplied to the compressor, in which it is again condensed by the pressure acting in the quenching zone. Finally, the repeated supply to the quenching zone is performed.

The above described example shows a possibility of implementing the inventive process. It is adjustable with respect to the temperature conditions in the quenching zone within a wide region, so that these temperature conditions can be adjusted to the design and capacity of the waste heat boiler.

The above described method can also be used in a similar manner for producing a synthesis gas for other synthesis products than methanol, as long as the reaction conditions are adjusted so that the product gas has a volume ratio of carbon monoxide to water defined for the desired synthesis reaction.

It will be understood that each of the elements described above, or two or more together, may also find a useful application in other types of methods differing from the types described above.

While the invention has been illustrated and described as embodied in a method of producing methanol synthesis gas, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of producing a methanol synthesis gas with a ratio of carbon monoxide to hydrogen defined for a desired synthesis reaction, by gasifying of fine-grained to dust-like fuels at temperatures above a slag melting point, comprising the steps of producing a partial oxidation crude gas in a gasifier; indirectly cooling the produced partial oxidation crude gas in a waste heat boiler after the gasifier with steam generation; further cooling the partial oxidation gas after the waste boiler by adding a converted circulating gas; subjecting the thusly produced gas mixture of the partial oxidation gas with the converted circulating gas to a dry dedusting; separating the dedusted gas mixture into a product gas partial stream and a circulating gas partial stream; subjecting the product gas partial stream to a further cooling, a subsequent gas washing for removing residual dust and impurities, a final cooling for water condensation, and a desulfurization and $CO_2$ removal, and then recovering the desulfurized product methanol synthesis gas; saturating the circulating gas partial stream with use of a condensate from the final cooling of the product gas partial stream and washing at a dew point of the gas; subjecting the thusly purified circulating gas partial stream, for adjusting a molar ratio of carbon monoxide to hydrogen to a CO-conversion in the presence of a sulfur resistant catalyst; and cooling the converted circulating gas close to its water steam dew point for further cooling of the partial oxidation crude gas after the waste heat boiler by recycling the converted circulation gas for adding to the partial oxidation crude gas.

2. A method as defined in claim 1, wherein the circulating gas partial stream has x-time volume of the product gas partial stream, wherein $$x = \frac{1}{\mu} \frac{\left(\frac{1}{r_s} + 1\right)}{\left(\frac{1}{r} + 1\right)} - 1$$

wherein $\mu$ is CO-conversion value during the CO-conversion, r is a molar ratio of carbon monoxide to hydrogen in the partial oxidation crude gas and $r_s$ is a corresponding molar ratio in the methanol synthesis gas.

3. A method as defined in claim 1; and further comprising supplying the partial oxidation crude gas at temperatures between 600°–1,450° C. into a quenching zone and mixing it there with the converted circulating gas, so as to lower temperature of the produced gas mixture to a value between 200° and 800° C.

4. A method as defined in claim 3, wherein the partial oxidation crude gas is supplied to the quenching zone at temperature between 800° and 1,200° C., and the temperature of the produced gas mixture is lowered to between 300° and 450° C.

5. A method as defined in claim 1, wherein said CO-conversion of the circulating gas partial stream is performed so that between 60 and 95% of the supplied carbon monoxide is converted.

6. A method as defined in claim 5, wherein said CO-conversion of the circulating gas partial stream is performed so that between 80 and 95% of the supplied carbon monoxide is converted.

7. A method as defined in claim 1; and further comprising the steps of washing the product gas partial stream and the circulating gas partial stream with a same washing water circulation, including withdrawing a washing water partial stream from the wet washing of the circulating gas partial stream, cleaning the washing water partial stream and using the same for saturating the circulating gas partial stream.

8. A method as defined in claim 1; and further comprising the steps of continuously analytically monitoring a molar ratio of the carbon monoxide to hydrogen in the product gas partial stream, and during operational changes adjusting the x-value of the circulating gas to the product gas to a desired value.

9. A method as defined in claim 8, wherein said adjusting includes supplying a partial stream of the circulating gas in a quantity of 0.1 to 1.0 $Nm^3/kg$ carbon$_{wf}$ to burners of the gasifier through a central lance and using the same instead of water or steam for a temperature moderation during the gasifying.

10. A method as defined in claim 9, wherein said supplying a partial stream of the circulating gas includes supplying the partial stream of the circulating gas in a quantity of 0.3–0.6 $Nm^3/kg$.

11. A method of producing a synthesis gas with a ratio of carbon monoxide to hydrogen defined for a desired synthesis reaction, by gasifying of fine-grained to dust-like fuels at temperatures above a slag melting point, comprising the steps of producing a partial oxidation crude gas in a gasifier; indirectly cooling the produced partial oxidation crude gas in a waste heat boiler after the gasifier with steam generation; further cooling the partial oxidation gas after the waste boiler by adding a converted circulating gas; subjecting the thusly produced gas mixture of the partial oxidation gas with the converted circulating gas to a dry dedusting; separating the dedusted gas mixture into a product gas partial stream and a circulating gas partial stream; subjecting the product gas partial stream to a further cooling, a subsequent gas washing for removing residual dust and impurities, a final cooling for water condensation, and a desulfurization and $CO_2$ removal, and then recovering the desulfurized product gas, saturating the circulating gas partial stream with use of a condensate from the final cooling of the product gas partial stream and washing at a dew point of the gas; subjecting the thusly purified circulating gas partial stream, for adjusting a molar ratio of carbon monoxide to hydrogen to a CO-conversion in the presence of a sulfur resistant catalyst; and cooling the converted circulating gas close to its water steam dew point for further cooling of the partial oxidation crude gas after the waste heat boiler by recycling the converted circulation gas for adding to the partial oxidation crude gas.

* * * * *